(12) United States Patent
Majeed et al.

(10) Patent No.: US 11,925,671 B2
(45) Date of Patent: Mar. 12, 2024

(54) PROCESS AND COMPOSITIONS FOR ENHANCING ENERGY EXPENDITURE

(71) Applicants: Muhammed Majeed, Bangalore (IN); Kalyanam Nagabhushanam, East Windsor, NJ (US); Lakshmi Mundkur, Bangalore (IN); Mohammad Mansoor Ansari, Bangalore (IN)

(72) Inventors: Muhammed Majeed, Bangalore (IN); Kalyanam Nagabhushanam, East Windsor, NJ (US); Lakshmi Mundkur, Bangalore (IN); Mohammad Mansoor Ansari, Bangalore (IN)

( * ) Notice: Subject to any disclaimer, the term of this patent is extended or adjusted under 35 U.S.C. 154(b) by 0 days.

(21) Appl. No.: 17/151,124

(22) Filed: Jan. 16, 2021

(65) Prior Publication Data
US 2021/0220424 A1 Jul. 22, 2021

Related U.S. Application Data

(60) Provisional application No. 62/962,339, filed on Jan. 17, 2020.

(51) Int. Cl.
| | | |
|---|---|---|
| *A61K 36/8905* | (2006.01) | |
| *A61K 31/05* | (2006.01) | |
| *A61K 31/343* | (2006.01) | |
| *A61K 36/185* | (2006.01) | |
| *A61P 3/04* | (2006.01) | |

(52) U.S. Cl.
CPC .......... *A61K 36/8905* (2013.01); *A61K 31/05* (2013.01); *A61K 31/343* (2013.01); *A61K 36/185* (2013.01); *A61P 3/04* (2018.01); *A61K 2236/15* (2013.01); *A61K 2236/333* (2013.01); *A61K 2236/35* (2013.01); *A61K 2236/39* (2013.01); *A61K 2300/00* (2013.01)

(58) Field of Classification Search
None
See application file for complete search history.

(56) References Cited

U.S. PATENT DOCUMENTS 10,172,903 B2 * 1/2019 Majeed ................ A61K 31/343

FOREIGN PATENT DOCUMENTS

JP 2014172841 A * 9/2014

OTHER PUBLICATIONS

Deng (Latin American Journal of Pharmacy (2017), vol. 36, No. 3, pp. 590-594).*

* cited by examiner

*Primary Examiner* — Susan Hoffman (57) ABSTRACT

The invention discloses a composition comprising *Cyperus rotundus* extract and *Passiflora edulis* extract comprising piceatannol, scirpusin B, scirpusin A, cyperusphenol A and cyperusphenol B, standardized to contain 6-10% w/w total stilbenes. The invention also discloses the use of the above mentioned composition in enhancing energy expenditure in mammalian adipose cellular systems by the conversion of white adipose tissues to brown adipose tissues, inhibition of adipogenesis and for preventing weight gain in mammals.

3 Claims, 4 Drawing Sheets
(1 of 4 Drawing Sheet(s) Filed in Color)
Specification includes a Sequence Listing.

SEQUENCE LISTING

```
<160> NUMBER OF SEQ ID NOS: 10

<210> SEQ ID NO 1
<211> LENGTH: 21
<212> TYPE: DNA
<213> ORGANISM: ARTIFICIAL SEQUENCE
<220> FEATURE:
<223> OTHER INFORMATION: FORWARD PRIMER FOR UCP1

<400> SEQUENCE: 1
aggcttccag taccattagg t                                         21

<210> SEQ ID NO 2
<211> LENGTH: 22
<212> TYPE: DNA
<213> ORGANISM: ARTIFICIAL SEQUENCE
<220> FEATURE:
<223> OTHER INFORMATION: REVERSE PRIMER FOR UCP 1

<400> SEQUENCE: 2
ctgagtgagg caaagctgat tt                                        22

<210> SEQ ID NO 3
<211> LENGTH: 23
<212> TYPE: DNA
<213> ORGANISM: ARTIFICIAL SEQUENCE
<220> FEATURE:
<223> OTHER INFORMATION: FORWARD PRIMER FOR PGC1 ALPHA

<400> SEQUENCE: 3
tatggagtga catagagtgt gct                                       23

<210> SEQ ID NO 4
<211> LENGTH: 22
<212> TYPE: DNA
<213> ORGANISM: ARTIFICIAL SEQUENCE
<220> FEATURE:
<223> OTHER INFORMATION: REVERSE PRIMER FOR PGC1 ALPHA

<400> SEQUENCE: 4
ccacttcaat ccacccagaa ag                                        22

<210> SEQ ID NO 5
<211> LENGTH: 19
<212> TYPE: DNA
<213> ORGANISM: ARTIFICIAL SEQUENCE
```

```
<220> FEATURE:
<223> OTHER INFORMATION: FORWARD PRIMER FOR PRDM16

<400> SEQUENCE: 5
cagcacggtg aagccattc                                                   19

<210> SEQ ID NO 6
<211> LENGTH: 17
<212> TYPE: DNA
<213> ORGANISM: ARTIFICIAL SEQUENCE
<220> FEATURE:
<223> OTHER INFORMATION: REVERSE PRIMER FOR PRDM16

<400> SEQUENCE: 6
gcgtgcatcc gcttgtg                                                     17

<210> SEQ ID NO 7
<211> LENGTH: 19
<212> TYPE: DNA
<213> ORGANISM: ARTIFICIAL SEQUENCE
<220> FEATURE:
<223> OTHER INFORMATION: FORWARD PRIMER FOR BMP7

<400> SEQUENCE: 7
ccaaagaacc aagaggccc                                                   19

<210> SEQ ID NO 8
<211> LENGTH: 21
<212> TYPE: DNA
<213> ORGANISM: ARTIFICIAL SEQUENCE
<220> FEATURE:
<223> OTHER INFORMATION: REVERSE PRIMER FOR BMP7

<400> SEQUENCE: 8
gctgctgttt tctgccacac t                                                21

<210> SEQ ID NO 9
<211> LENGTH: 20
<212> TYPE: DNA
<213> ORGANISM: ARTIFICIAL SEQUENCE
<220> FEATURE:
<223> OTHER INFORMATION: FORWARD PRIMER FOR BETA ACTIN

<400> SEQUENCE: 9
gaagtccctc accctcccaa                                                  20

<210> SEQ ID NO 10
<211> LENGTH: 16
<212> TYPE: DNA
<213> ORGANISM: ARTIFICIAL SEQUENCE
<220> FEATURE:
<223> OTHER INFORMATION: REVERSE PRIMER FOR BETA ACTIN

<400> SEQUENCE: 10
ggcatggacg cgacca                                                      16
```

PROCESS AND COMPOSITIONS FOR ENHANCING ENERGY EXPENDITURE

CROSS-REFERENCE TO RELATED PATENT APPLICATIONS

This is a non-provisional US patent application claiming priority from U.S. Provisional application 62/962,339, filed on 17 Jan. 2020, the details of which are being incorporated herein by reference.

FILED OF INVENTION

The present invention relates to composition for enhancing energy expenditure. More specifically, the invention pertains to compositions comprising *Cyperus rotundus* extract and *Passiflora edulis* extract for increasing energy expenditure in mammalian cells by conversion of WAT to BAT.

BACKGROUND OF THE INVENTION

Obesity is considered to be the leading health risk for the development of various disorders like hypertension, type 2 diabetes, heart disease, stroke, osteoarthritis, and mental illness. Globally, more than 1 in 10 individuals are obese and about 36% of American adults are obese (https://www.medicalnewstoday.com/articles/319902.php, accessed on 10 May 2018). Obesity results due to imbalance between the energy content of food eaten and energy expended by the body to maintain life and to perform physical work. Such an energy balance framework is a potentially powerful tool for investigating the regulation of body weight.

The conversion of white adipose tissue (WAT) to brown adipose tissue (BAT), or termed as "browning" of WAT, is now garnering more attention to enhance energy expenditure. While, WAT serves as a store house of energy, BAT lipids serve primarily as fuel for oxidative phosphorylation, primarily depending on UCP1 activity and increases energy expenditure by the production of ATP. BAT is also involved in heat production and helps in maintaining an adequate core body temperature. BAT also has deeper roles in the mammalian body system like Norepinephrine-induced thermogenesis, Metaboloregulatory Thermogenesis, as a secretory organ, in effective glucose and lipid clearance, Hibernation and Arousal etc. (Cannon et al., Physiol Rev 84: 277-359, 2004). Thus BAT, plays an important role in maintaining energy homeostasis.

In various instances, wherein energy expenditure is essential like in obesity, metabolic disorders, diabetes, cold thermogenesis, sports endurance etc, change from WAT to BAT is crucial for the maintenance of an effective energy homeostasis. Plant based dietary compounds have been reported to promote BAT activation and WAT browning. The role of brown adipose tissue (BAT) is well described in the following prior arts:
1. Hadi et al, Front. Physiol., 11 Jan. 2019, doi: https://doi.org/10.3389/fphys.2018.01954
2. Elattar. S and Satyanarayana, "Can Brown Fat Win the Battle against White Fat?", J Cell Physiol. 2015 October; 230(10):2311-7
3. Zafrir B, "Brown adipose tissue: research milestones of a potential player in human energy balance and obesity", Horm Metab Res. 2013 October; 45(11):774-85
4. Giralt M, Villarrova F "White, brown, beige/brite: different adipose cells for different functions?" Endocrinology. 2013 September; 154(9):2992-3000

Drugs and/or natural molecules that facilitate the conversion of white to brown adipocytes are effective in the treatment/management of obesity related conditions. US patent publication no. 20150238438 discloses a composition comprising extract of *Cyperus rotundus* rhizomes standardized to contain 5% of total stilbenes, consisting essentially of a combination of Piceatannol, Scirpusin B and Scirpusin A for the management of obesity. US patent publication no. 20190328818 discloses a composition comprising *Cyperus rotundus* extract, Garcinia extract and *Coleus forskohlii* extract for tire management of obesity. However, the prior art documents fail to address the issue of maintaining energy homeostasis which is important in managing many disease conditions including obesity. Further, we need a better understanding of the components involved in energy expenditure and their interactions over various time scales to explain the natural history of conditions such as obesity and to estimate the magnitude and potential success of therapeutic interventions. (Kevin D. Hall, Steven B. Heymsfield, Joseph W. Kemnitz, Samuel Klein, Dale A. Schoeller, and John R. Speakman, Energy balance and its components: implications for body weight regulation, Am J Clin Nutr. 2012 April; 95(4): 989-994). The present invention solves the above problem by disclosing a composition comprising *Cyperus rotundus* extract and *Passiflora edulis* extract standardised to contain Piceatannol, Scirpusin B and Scirpusin A, Cyperusphenol A and Cyperusphenol B for enhancing energy expenditure.

The principle object of the invention is to disclose a composition comprising *Cyperus rotundus* extract and *Passiflora edulis* extract comprising Piceatannol, Scirpusin B and Scirpusin A, and Cyperusphenols, standardized to contain 6-10% w/w total stilbenes and the process of formulating the composition.

It is another object of the invention to disclose a method of enhancing energy expenditure in mammalian adipose cellular systems using a composition comprising *Cyperus rotundus* extract and *Passiflora edulis* extract comprising Piceatannol, Scirpusin B, Scirpusin A and Cyperusphenols, standardized to contain 6-10% w/w total stilbenes.

It is yet another object of the invention to disclose a method of therapeutic management of obesity in mammals using a composition comprising *Cyperus rotundus* extract and *Passiflora edulis* extract comprising Piceatannol, Scirpusin B, Scirpusin A and Cyperusphenols, standardized to contain 6-10% w/w total stilbenes.

The present invention fulfils the above mentioned objectives and provides further related advantages.

SUMMARY OF THE INVENTION

In a most preferred embodiment, the invention discloses a composition comprising *Cyperus rotundus* extract and *Passiflora edulis* extract comprising Piceatannol, Scirpusin B, Scirpusin A, Cyperusphenol A and Cyperusphenol B, standardized to contain 6-10% w/w total stilbenes.

In a preferred embodiment, the invention discloses a method of enhancing energy expenditure in mammalian adipose cellular systems, said method comprising: step of bringing into contact mammalian pre-adipocytes or adipocytes into contact with a composition comprising *Cyperus rotundus* extract and *Passiflora edulis* extract comprising Piceatannol, Scirpusin B, Scirpusin A Cyperusphenol A and Cyperusphenol B, standardized to contain 6-10% w/w total stilbenes to achieve effects of (a) increased expression of genes and proteins that function individually or in combination to specifically recruit brown adipocytes or beige or brite adipocytes, (b) induce brown or beige or brite like phenotype in white adipocyte depots, (c) induce enhanced expression of mitochondrial uncoupling protein-1 to result in increased mitochondrial thermogenesis in differentiated brown adipocytes and beige or brite adipocytes.

In another preferred embodiment, the invention discloses a method of inhibition of adipogenesis in mammalian cellular systems, said method comprising step of bringing into contact mammalian adipocytes into contact with a composition comprising *Cyperus rotundus* extract and *Passiflora edulis* extract comprising Piceatannol, Scirpusin B, Scirpusin A Cyperusphenol A and Cyperusphenol B, standardized to contain 6-10% w/w total stilbenes to bring about inhibition in adipogenesis.

In another preferred embodiment, the invention discloses a method for therapeutic management of obesity in mammals, said the method comprising steps of administering an effective concentration of a composition comprising *Cyperus rotundus* extract and *Passiflora edulis* extract comprising Piceatannol, Scirpusin B, Scirpusin A Cyperusphenol A and Cyperusphenol B, standardized to contain 6-10% w/w total stilbenes to said mammals to bring about prevention in weight gain.

Other features and advantages of the present invention wall become apparent from the following more detailed description, taken in conjunction with the accompanying images, which illustrate, by way of example, the principle of the invention.

DESCRIPTION OF DRAWINGS

The patent or application file contains at least one drawing executed in color. Copies of this patent or patent application publication with color drawing(s) will be provided by the office upon request and payment of the necessary fee.

DESCRIPTION OF PREFERRED EMBODIMENTS

In a most preferred embodiment, the invention discloses a composition comprising *Cyperus rotundus* extract and *Passiflora edulis* extract comprising Piceatannol, Scirpusin B, Scirpusin A, Cyperusphenol A and Cyperusphenol B, standardized to contain 6-10% w/w total stilbenes. In another related embodiment, the *Cyperus rotundus* extract is standardized to contain 0.1-5% total stilbenes and *Passiflora edulis* extract is standardized to contain 15-25% total stilbenes. In a related embodiment, the *Cyperus rotundus* extract and *Passiflora edulis* extract are in the ratios ranging from 1:5 to 5:1. In a related embodiment, Cyperusphenol A include both the meso and dl isomers since these co-occur in *Cyperus rotundus* as described by T Ito, H Endo, H Shinohara, M Oyama, Y Akao and M Iinuma, Fitoterapia 83, 1420-1429 (2012)

In another preferred embodiment, the composition comprising *Cyperus rotundus* extract and *Passiflora edulis* extract is obtained by the process comprising steps of
 a) Powdering tubers of *Cyperus rotundus* into a fine mesh
 b) Refluxing with 4 volumes of methanol and heating at 65-70° C. for 3-4 hours and filtering the solution to obtain a clear extract;
 c) Repeating the process of step b) twice and combining the three extracts;
 d) Concentrating the extract of step c) to obtain as extract containing 0.1-5% total stilbenes.
 e) Powdering seeds of *Passiflora edulis* into a fine mesh
 f) Refluxing with 4 volumes of hexane and heating at 65-70° C. for 3-4 hours and filtering the solution;
 g) Repeating the process of step f) twice and combining the three hexane extracts;
 h) Concentrating the combined extract of step g) by distilling the solvent to obtain a clear Marc;
 i) Adding 4 volumes of ethanol to the Marc of step h) and heating at 70-75° C. and filtering;
 j) Repeating the process of step i) twice and combining the three ethanol extracts to obtain a clear ethanol extract of the *Passiflora edulis* seeds;
 k) Dissolving the ethanol extract of step j) in 6 volumes of water;
 l) Charging with 6 volumes of ethyl acetate and stirring for 5 minutes and allowing to settle for 1 hour;
 m) Collecting the ethyl acetate layer and washing with water;
 n) Repeating the process of steps 1) and m) two more times and combining all ethyl acetate layers;
 o) Concentrating the ethyl acetate layer by heating at 65-75° C. to obtain *Passiflora edulis* seed extract containing 15-25% total stilbenes.
 p) Mixing the *Cyperus rotundus* extract and *Passiflora edulis* seed extract in the ratios of 1:5, 2:4, 3:3, 4:2, and 5:1 respectively to obtain a composition comprising *Cyperus rotundus* extract and *Passiflora edulis* extract comprising Piceatannol, Scirpusin B, Scirpusin A Cyperusphenol A and Cyperusphenol B, standardized to contain 6-10% w/w total stilbenes.

In another related embodiment, the composition is formulated with pharmaceutically/nutraceutically acceptable excipients, adjuvants, diluents or carriers and administered orally in the form of tablets, capsules, syrups, gummies, powders, suspensions, emulsions, chewables, candies and eatables.

In a preferred embodiment, the invention discloses a method of enhancing energy expenditure in mammalian adipose cellular systems, said method comprising: step of bringing into contact mammalian pre-adipocytes or adipocytes into contact with a composition comprising *Cyperus rotundus* extract and *Passiflora edulis* extract comprising Piceatannol, Scirpusin B, Scirpusin A Cyperusphenol A and Cyperusphenol B, standardized to contain 6-10% w/w total stilbenes to achieve effects of (a) increased expression of genes and proteins that function individually or in combination to specifically recruit brown adipocytes or beige or brite adipocytes, (b) induce brown or beige or brite like phenotype in white adipocyte depots, (c) induce enhanced expression of mitochondrial uncoupling protein-1 to result in increased mitochondrial thermogenesis in differentiated brown adipocytes and beige or brite adipocytes. In a related embodiment, the genes and proteins are at least one factor selected from the group consisting of comprising PRDM16, PGC-1α and BMP7. In a related embodiment, enhancing energy expenditure is essential in conditions selected from the group consisting of, but not Limited to, obesity, metabolic disorders, diabetes, cold thermogenesis and sports endurance In another preferred embodiment, the invention discloses a composition comprising *Cyperus rotundus* extract and *Passiflora edulis* extract comprising Piceatannol, Scirpusin B, Scirpusin A CyperusphenolCyperusphenol A and Cyperusphenol B, standardized to contain 6-10% w/w total stilbenes for use in enhancing energy expenditure in mammalian preadipocytes or adipocytes by administering in effective amounts targeted towards mammalian pre-adipocytes to bring about the effects of (a) increased expression of genes and proteins that function individually or in combination to specifically recruit brown adipocytes or beige or brite adipocytes, (b) induce brown or beige or brite like phenotype in white adipocyte depots, (c) induce enhanced expression of mitochondrial uncoupling protein-1 to result in increased mitochondrial thermogenesis in differentiated brown adipocytes and beige or brite adipocytes. In a related embodiment, the genes and proteins are at least one factor selected from the group consisting of comprising PRDM16, PGC-1α and BMP7. In a related embodiment, enhancing energy expenditure is essential in conditions selected from the group consisting of, but not limited to, obesity, metabolic disorders, diabetes, cold thermogenesis and sports endurance.

In a preferred embodiment, the invention discloses a method of inhibition of adipogenesis in mammalian cellular systems, said method comprising step of bringing into contact mammalian adipocytes into contact with a composition comprising *Cyperus rotundus* extract and *Passiflora edulis* extract comprising Piceatannol, Scirpusin B, Scirpusin A Cyperusphenol A and Cyperusphenol B, standardized to contain 6-10% w/w total stilbenes to bring about inhibition in adipogenesis.

In yet another preferred embodiment, the invention discloses a composition comprising *Cyperus rotundus* extract and *Passiflora edulis* extract comprising Piceatannol, Scirpusin B, Scirpusin A Cyperusphenol A and Cyperusphenol B, standardized to contain 6-10% w/w total stilbenes use in inhibiting adipogenesis in mammalian adipocytes.

In another preferred embodiment, the invention discloses a method for therapeutic management of obesity in mammals, said the method comprising steps of administering an effective concentration of a composition comprising *Cyperus rotundus* extract and *Passiflora edulis* extract comprising Piceatannol, Scirpusin B, Scirpusin A Cyperusphenol A and Cyperusphenol B, standardized to contain 6-10% w/w total stilbenes to said mammals to bring about prevention in weight gain.

In another preferred embodiment, the invention discloses a composition comprising *Cyperus rotundus* extract and *Passiflora edulis* extract comprising Piceatannol, Scirpusin B, Scirpusin A Cyperusphenol A and Cyperusphenol B, standardized to contain 6-10% w/w total stilbenes for preventing weight gain in mammals. In another related embodiment, the composition is formulated with pharmaceutically/nutraceutically acceptable excipients, adjuvants, diluents or carriers and administered orally in the form of tablets, capsules, syrups, gummies, powders, suspensions, emulsions, chewables, candies and eatables.

The aforesaid most preferred embodiments incorporating the technical features and technical effects of instant invention, are explained through illustrative examples herein under.

Example 1: Isolation and Formulation of Composition

The composition comprising *Cyperus rotundus* extract and *Passiflora edulis* extract is obtained by the process comprising steps of
a) Powdering tubers of *Cyperus rotundus* into a fine mesh
b) Refluxing with 4 volumes of methanol and heating at 65-70° C. for 3-4 hours and filtering the solution to obtain a clear extract;
c) Repeating the process of step b) twice and combining the three extracts;
d) Concentrating the extract of step c) to obtain as extract containing 0.1-5% total stilbenes.
e) Powdering seeds of *Passiflora edulis* into a fine mesh
f) Refluxing with 4 volumes of hexane and heating at 65-70° C. for 3-4 hours and filtering the solution;
g) Repeating the process of step f) twice and combining the three hexane extracts;
h) Concentrating the combined extract of step g) by distilling the solvent to obtain a clear Marc;
i) Adding 4 volumes of ethanol to the Marc of step h) and heating at 70-75° C. and filtering;
j) Repeating the process of step i) twice and combining the three ethanol extracts to obtain a clear ethanol extract of the *Passiflora edulis* seeds;
k) Dissolving the ethanol extract of step j) in 6 volumes of water;
l) Charging with 6 volumes of ethyl acetate and stirring for 5 minutes and allowing to settle for 1 hour;
m) Collecting the ethyl acetate layer and washing with water;
n) Repeating the process of steps 1) and m) two more times and combining all ethyl acetate layers;
o) Concentrating the ethyl acetate layer by heating at 65-75° C. to obtain *Passiflora edulis* seed extract containing 15-25% total stilbenes.
p) Mixing the *Cyperus rotundus* extract and *Passiflora edulis* seed extract in the ratios of 1:5, 2:4, 3:3, 4:2, and 5:1 respectively to obtain a composition comprising *Cyperus rotundus* extract and *Passiflora edulis* extract comprising Piceatannol, Scirpusin B, Scirpusin A Cyperusphenol A and Cyperusphenol B, standardized to contain 6-10% w/w total stilbenes.

As an illustrative example, the *Cyperus rotundus* extract and *Passiflora edulis* seed extract are mixed in the ratios of 2:1 respectively to obtain a composition comprising *Cyperus rotundus* extract and *Passiflora edulis* extract comprising Piceatannol, Scirpusin B, Scirpusin A Cyperusphenol A and Cyperusphenol B, standardized to contain 7% w/w total stilbenes.

Example 2: Adipogenesis Inhibition and Brown Fat Specific Gene Expression by *Cyperus rotundus* Extract and *Passiflora edulis* Extract in Cultured 3T3L1

Cell Culture

Mouse 3T3-L1 mouse embryo fibroblasts (American Type Culture Collection (ATCC, Rockville, Md., USA) were cultured in DMEM containing 25 mM glucose with 10% heat-inactivated fetal calf serum with antibiotics at 37° C. and 5% CO2. When the cells were 70-80% confluent, they were trypsinized, washed and seeded in 6 well plates at a density of $2\times10^6$ cells per well. Cells were induced to differentiate 2 d after reaching confluence (day 0), by supplementing DMEM media containing 10% Fetal Bovine Serum (FBS) along with 1 μg/mL insulin, 0.25 μM dexamethasone, 0.5 mM 1-methyl-3-isobutyl-xanthine (IBMX) and different concentrations of *Cyperus rotundus* extract and *Passiflora edulis* extract comprising Piceatannol, Scirpusin B, Scirpusin A Cyperusphenol A and Cyperusphenol B, standardized to contain 6-10% w/w total stilbenes (Composition 1—with tradename CIRPUSINS®) or *Cyperus* extract standardized to contain 3-5% w/w total stilbenes (Composition 2—CRE) at different concentrations. The composition comprising Piceatannol, Scirpusin B, Scirpusin A Cyperusphenol A and Cyperusphenol B, standardized to contain 6-10% w/w total stilbenes is trademarked as CIRCPUSINS®. From day 3 until day 7, cells were maintained in progression media supplemented with 1 μg/mL insulin and different concentrations of the composition comprising CIRPUSINS®, compared to Composition 2—CRE. Untreated cells and undifferentiated cells grown in FCS media were taken as A positive and negative controls for the experiment. To study inhibition of adipogenesis, cells were plated in 48 well plate at a density of 10000 cells per well and differentiated as mentioned earlier. Quantification for amount of triglycerides accumulated in adipocytes was done by Oil red O staining Cell viability was measured using sulforhodamine-B (SRB) assay (Orellana & Kasinski, 2016, Assay in Cell Culture to Investigate Cell Proliferation. Bio Protoc. 2016 Nov. 5; 6(21):e1984. doi: 10.21769/BioProtoc. 1984).

RNA Extraction and qRT-PCR

RNA was extracted from 3T3-L1 cells using the trizol method and treated with DNAse to remove any traces of DNA (Au-Tan, Au-Pepin, & Au-Lavoie, 2018). First-strand cDNA was prepared from RNA samples using oligo dT primers and Superscript III reverse transcriptase (cDNA synthesis kit, Invitrogen™). Quantitative real-time PCR (qRT-PCR) was performed with SYBR Green I fluorescent dye using Light cycler 96'1 according to the manufacturer's instructions (Light Cycler® FastStart DNA Master SYBR Green I, Roche). The β-actin gene was used as the housekeeping gene. The following primers were used;

UCP1
F-AGGCTTCCAGTACCATTAGGT

R-CTGAGTGAGGCAAAGCTGATTT

PGC1α
F-TATGGAGTGACATAGAGTGTGCT

R-CCACTTCAATCCACCCAGAAAG

PRDM16
F-CAGCACGGTGAAGCCATTC

R-GCGTGCATCCGCTTGTG

BMP7
F-CCAAAGAACCAAGAGGCCC

R-GCTGCTGTTTTCTGCCACACT

β-Actin
F-GAAGTCCCTCACCCTCCCAA

R-GGCATGGACGCGACCA

Gene Expression for Adipocyte Browning

Figure 1A:
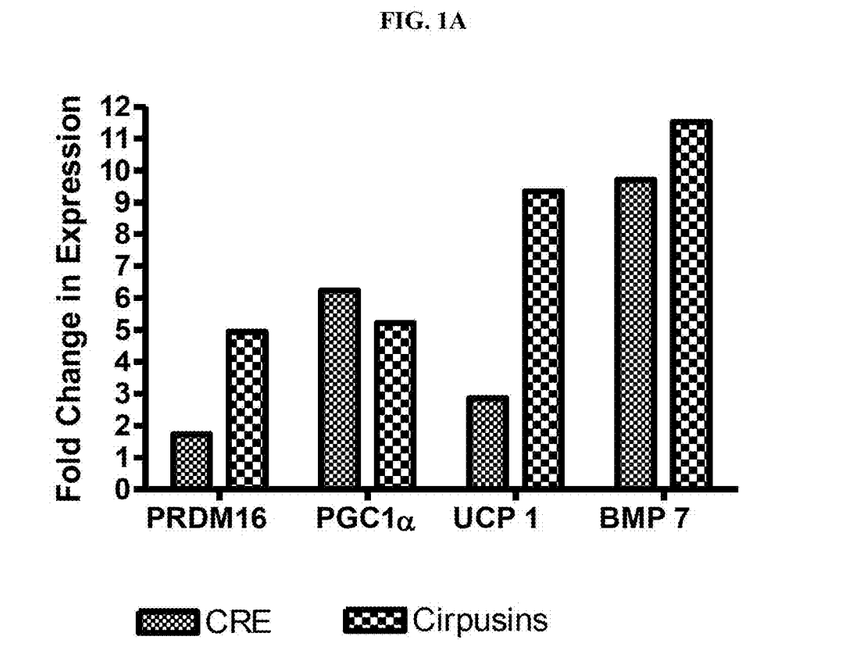
FIG. 1A is a graphical representation showing the increase in expression of genes related to brown fat conversion in mouse 3T3-L1 pre-adipocytes administered with composition comprising *Cyperus rotundus* extract and *Passiflora edulis* extract comprising Piceatannol, Scirpusin B, Scirpusin A Cyperusphenol A and Cyperusphenol B, standardized to contain 6-10% w/w total stilbenes at 3.125 µg/ml.
Figure 1B:
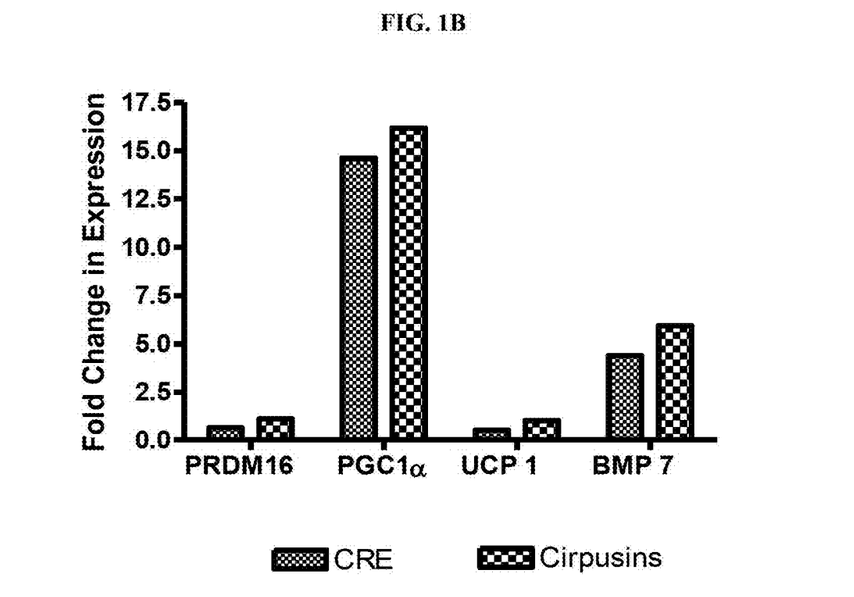
FIG. 1B is a graphical representation showing the increase in expression of genes related to brown fat conversion in mouse 3T3-L1 pre-adipocytes administered with composition comprising *Cyperus rotundus* extract and *Passiflora edulis* extract comprising Piceatannol, Scirpusin B, Scirpusin A Cyperusphenol A and Cyperusphenol B, standardized to contain 6-10% w/w total stilbenes at 6.25 µg/ml.

The mRNA levels of transcripts associated with energy metabolism (PGC-1α), factors causing adipocyte browning (PRDM16), and secretary protein inducing BAT differentiation (BMP7), were assessed in the compositions treated cells compared to control. Fold change in expression was calculated in comparison to untreated differentiated cells, using the DDCT method Results Gene Expression The fold change in the expression of genes related to BAT, compared between CUE (*Cyperus* extract) and Cirpusins (Composition of Instant invention) are presented in FIGS. 1A (at 3.125 μg/ml) and 1B (at 6.25 μg/ml). The results indicated that the fold change in the expression of genes in cells treated with CIRPUSINS was better compared to CRE (*Cyperus rotundus* extract standardized to contain 3-5% total stilbenes) (TABLE 1), indicating that the composition comprising *Cyperus rotundus* extract and *Passiflora edulis* extract comprising Piceatannol, Scirpusin B, Scirpusin A Cyperusphenol A and Cyperusphenol B, standardized to contain 6-10% w/w total stilbenes, performs better in increased energy expenditure compared to *Cyperus rotundus* extract standardized to contain 3-5% total stilbenes. Thus, further studies of adipogenesis inhibition and preventing weigh gain in mammals were carried out for the composition comprising *Cyperus rotundus* extract and *Passiflora edulis* extract comprising Piceatannol. Scirpusin B. Scirpusin A Cyperusphenol A and Cyperusphenol B, standardized to contain 6-10% w/w total stilbenes.

TABLE 1

Fold Change in expression compared to differentiated and untreated cells

| Sample | Concentration (μg/ml) | PRDM16 | PGC1 ALPHA | UCP 1 | BMP 7 |
|---|---|---|---|---|---|
| CRE | 3.125 | 0.65 | 14.62 | 0.53 | 4.38 |
|  | 6.25 | 1.73 | 6.23 | 2.87 | 9.71 |
| CIRPUSINS | 3.125 | 1.11 | 16.17 | 1.03 | 5.94 |
|  | 6.25 | 4.94 | 5.21 | 9.35 | 11.51 |

Figure 2A:
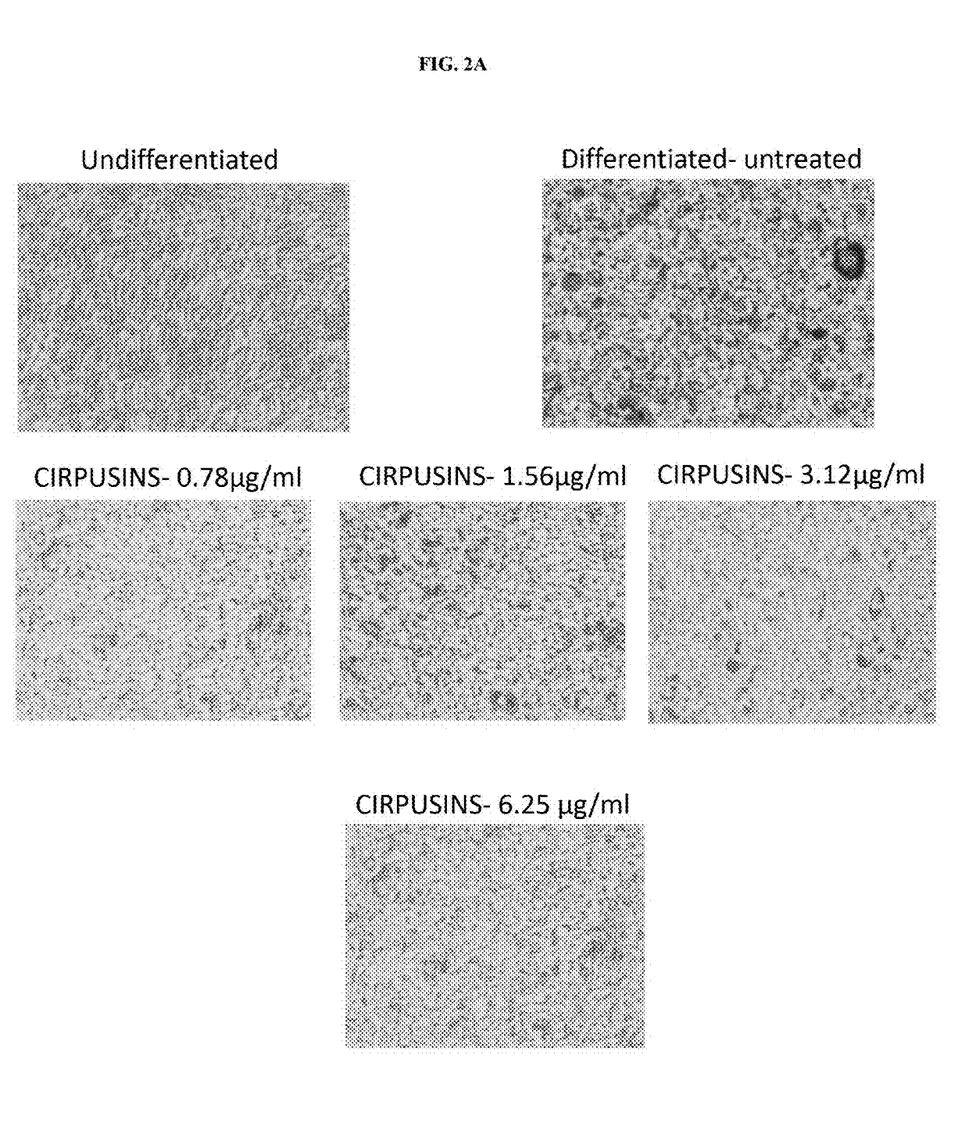
FIG. 2A is the oil-O-red staining of adipocytes indicating a dose dependent reduction in lipid accumulation in adipocytes by comprising *Cyperus rotundus* extract and *Passiflora edulis* extract comprising Piceatannol, Scirpusin B, Scirpusin A Cyperusphenol A and Cyperusphenol B, standardized to contain 6-10% w/w total stilbenes.
Figure 2B:
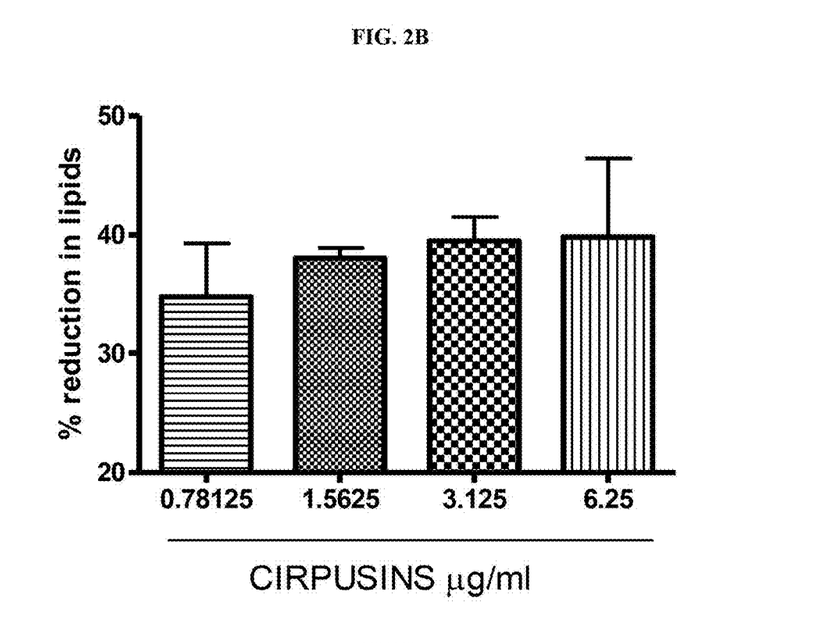
FIG. 2B is the graphical representation of the percentage inhibition of adipogenesis by composition comprising *Cyperus rotundus* extract and *Passiflora edulis* extract comprising Piceatannol, Scirpusin B, Scirpusin A Cyperusphenol A and Cyperusphenol B, standardized to contain 6-10% w/w total stilbenes.

The composition comprising *Cyperus rotundus* extract and *Passiflora edulis* extract comprising Piceatannol, Scirpusin B, Scirpusin A Cyperusphenol A and Cyperusphenol B, standardized to contain 6-10% w/w total stilbenes showed a dose dependant inhibition of adipogenesis (FIGS. 2A and 2B)

Example 3: Anti-Obesity Studies

Methods

| | |
|---|---|
| Test system: Animal Species | Mice |
| Strain | C57 |
| Sex | Male |
| Justification for selection of species | C57 Mice are recommended species for conducting pharmacological study especially anti-obesity among the rodents and hence Anti-obesity study has been carried out in C57 Mice models. |
| No. of animals/group | 8 animals/Group. |
| Body weight range at receipt | 15-20 g |
| Age at treatment | 6-8 weeks |

Animals were housed under standard laboratory conditions, air-conditioned with adequate fresh air supply (12-15 Air changes per hour), room temperature 20.2-23.5° C. and relative humidity 58-64% with 12 hours fluorescent light and 12 hours dark cycle. The temperature and relative humidity was recorded once daily. Maximum of four animals were housed in a standard polypropylene cage with stainless steel mesh top grill having facilities for holding food and drinking water in water bottled fitted with stainless steel sipper tube. Clean sterilized paddy husk was provided as bedding material.

The animals were fed with Normal diet (Group-I) and High fat diet (Group-II to V) throughout the acclimatization and experimental period. Water was provided along with High Fat Diet to the animals throughout the acclimatization and experimental period. Water from water filter cum purifier was provided in animal feeding bottle with stainless steel sipper tubes.

Study Groups

TABLE 2

Groups for anti-obesity studies

| Groups | Treatment |
|---|---|
| G1 - Control | Mice were fed with Normal diet for 120 Days. |
| G2 - HFD | Mice were fed with high fat diet for 120 Days. |
| G3 - HFD + CIRPUSINS (50 mg/kg body weight) | Mice were fed with high fat diet for 16 weeks were administered with Cyprus extract (50 mg/kgbw) for 120 Days. |
| G4 - HFD + CIRPUSINS (100 mg/kg body weight) | Mice were fed with high fat diet for 16 weeks were administered with Cyprus extract (100 mg/kgbw) for 120 Days. |
| GS - HFD + CIRPUSINS (200 mg/kg body weight) | Mice were fed with high fat diet for 16 weeks and the mice were administered with Cyprus extract (200 mg/kgbw) for 120 Days. |

Body weight of the animals was recorded in all the days of experimental period. At the end of the experimental period, the animals were sacrificed by cervical dislocation. Blood was collected. Serum was separated by centrifugation and used for the analysis of biochemical parameters. The organs such as Liver and Fat Pads (Retroperitoneal, Perigonadal and Mesenteric) were dissected out and washed in phosphate buffered saline.

The following parameters were studied:
1. Measurement of Body weight
2. Estimation of Blood Glucose (GOD/POD Method)
3. Estimation of Uric acid (URICASE/POD Method)
4. Estimation of AST (Enzyme Kinetic Method)
5. Estimation of ALT (Enzyme Kinetic Method)
6. Estimation of Cholesterol (CHOD/POD Method)
7. Estimation of Triglycerides (GPO/POD Method)
8. Estimation of HDL Cholesterol (HDL Cholesterol Direct Reagent Kit, Beacon)
9. Determination of LDL Cholesterol (LDL Cholesterol Direct Reagent Kit, Beacon)

Results

Figure 3:
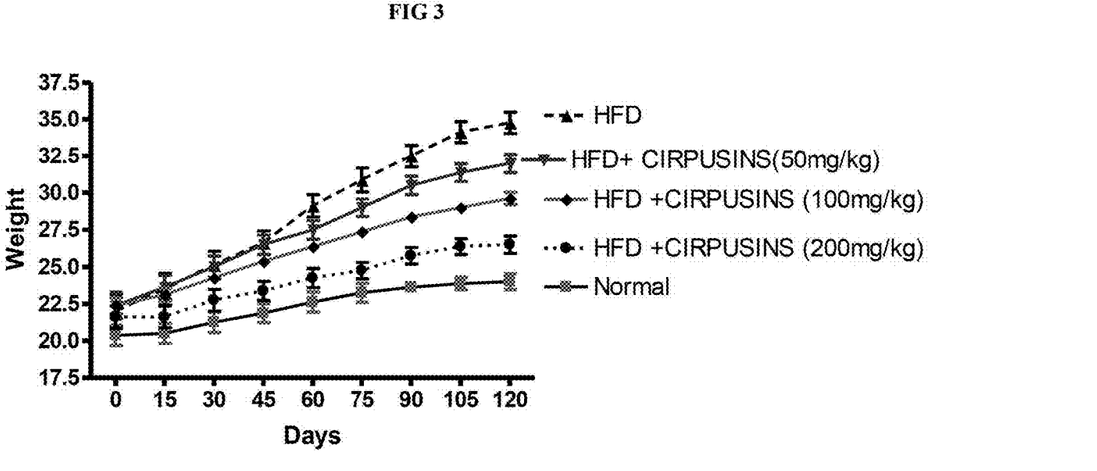
FIG. 3 is a graphical representation showing the weight gain in animals administered with different concentrations of composition comprising *Cyperus rotundus* extract and *Passiflora edulis* extract comprising Piceatannol, Scirpusin B, Scirpusin A Cyperusphenol A and Cyperusphenol B, standardized to contain 6-10% w/w total stilbenes over a period of 120 days.
Figure 4:
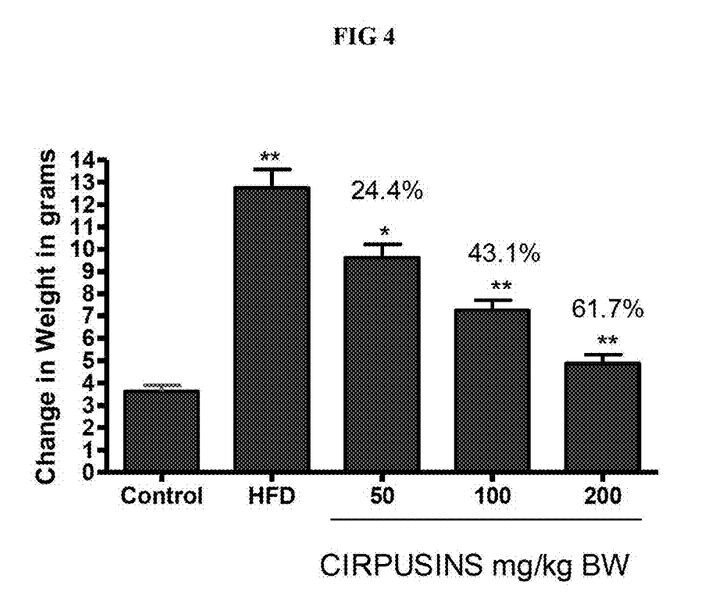
FIG. 4 is a graphical representation showing the change in weight of animals administered with different concentrations of composition comprising *Cyperus rotundus* extract and *Passiflora edulis* extract comprising Piceatannol, Scirpusin B, Scirpusin A Cyperusphenol A and Cyperusphenol B, standardized to contain 6-10% w/w total stilbenes over a period of 120 days.

The composition showed a dose dependant decrease in the body weight of the mice (FIG. 3 and FIG. 4). The weight gain induced by high fat diet was significantly reduced by the composition. At the highest dose of 200 mg/kg bw, the reduction was 61.7%

Significant reduction in retroperitoneal, perigonadal and mesenteric fat was also observed in the animals treated with the composition.

TABLE 3

Visceral fat weights in mice treated with CIRPUSINS

| | Retroperitoneal Fat (g wet tissue) | Perigonadal Fat (g wet tissue) | Mesenteric Fat (g wet tissue) |
|---|---|---|---|
| G1 - Control | 0.308 ± 0.01 | 0.413 ± 0.01 | 0.350 ± 0.02 |
| G2 - HFD | 0.848 ± 0.05 | 1.208 ± 0.09 | 0.837 ± 0.01 |
| G3 - HFD + CIRPUSINS (50 mg/kg body weight) | 0.817 ± 0.04 | 1.073 ± 0.03 | 0.784 ± 0.24 |
| G4 - HFD + CIRPUSINS (100 mg/kg body weight) | 0.606 ± 0.06 | 0.869 ± 0.03 | 0.595 ± 0.03 |
| G5 - HFD + CIRPUSINS (200 mg/kg body weight) | 0.417 ± 0.03 | 0.557 ± 0.01 | 0.388 ± 0.01 |

Among the biochemical parameters, the CIRPUSINS composition improved the lipid profile by decreasing the elevated levels of total cholesterol, LDL and triglycerides and increasing HDL cholesterol (Table 4)

TABLE 4

Lipid profile

| Groups | Cholesterol | HDL (mg/dl) | LDL (mg/dl) | TG (mg/dl) |
|---|---|---|---|---|
| G1 - Control | 83.88 ± 2.75 | 64.38 ± 2.92 | 6.73 ± 0.37 | 105.63 ± 2.00 |
| G2 - HFD | 190.63 ± 2.62 | 24.38 ± 2.77 | 76.45 ± 2.69 | 234.38 ± 2.67 |
| G3 - HFD + CIRPUSINS (50 mg/kg body weight) | 182.13 ± 2.75 | 26.63 ± 1.69 | 69.69 ± 3.34 | 178.25 ± 2.49 |
| G4 - HFD + CIRPUSINS (100 mg/kg body weight) | 169.63 ± 2.97 | 35.25 ± 2.49 | 43.48 ± 2.02 | 159.63 ± 2.67 |
| G5 - HFD + CIRPUSINS (200 mg/kg body weight) | 94.75 ± 2.82 | 55.50 ± 2.56 | 20.08 ± 0.67 | 126.38 ± 2.62 |

The composition also improved the elevated levels of glucose, Uric acid, and the liver enzymes (table 5)

TABLE 5

Biochemical parameters

| Groups | Glucose (mg/dl) | Uric Acid (mg/dl) | AST(U/L) | ALT(U/L) |
|---|---|---|---|---|
| G1 - Control | 89.50 ± 3.82 | 4.06 ± 0.16 | 30.50 ± 2.45 | 25.50 ± 1.51 |
| G2 - HFD | 153.13 ± 3.00 | 5.91 ± 0.24 | 53.38 ± 3.81 | 54.25 ± 1.67 |

TABLE 5-continued

Biochemical parameters

| Groups | Glucose (mg/dl) | Uric Acid (mg/dl) | AST(U/L) | ALT(U/L) |
|---|---|---|---|---|
| G3 - HFD + CIRPUSINS (50 mg/kg body weight) | 148.50 ± 2.45 | 5.49 ± 0.31 | 43.25 ± 2.87 | 48.75 ± 1.04 |
| G4 - HFD + CIRPUSINS (100 mg/kg body weight) | 123.00 ± 3.82 | 5.34 ± 0.27 | 38.38 ± 2.67 | 41.25 ± 1.04 |
| G5 - HFD + CIRPUSINS (200 mg/kg body weight) | 92.38 ± 3.11 | 4.63 ± 0.27 | 31.38 ± 1.06 | 34.75 ± 1.67 |

Overall, The results suggest that comprising *Cyperus rotundus* extract and *Passiflora edulis* extract comprising Piceatannol, Scirpusin B, Scirpusin A Cyperusphenol A and Cyperusphenol B, standardized to contain 6-10% w/w total stilbenes (CIRPUSINS®) is efficacious in controlling obesity in animals.

Other modifications and variations of the invention will be apparent to those skilled in the art from the foregoing disclosure and teachings. Thus, while only certain embodiments of the invention have been specifically described herein, it will be apparent that numerous modifications may be made thereto without departing from the spirit and scope of the invention and is to be interpreted only in conjunction with the appended claims.

We claim:

1. A method of enhancing energy expenditure in adipose cellular systems of a mammal, said method comprising a) identifying a mammal requiring increase in energy expenditure, and b) administering a composition comprising *Cyperus rotundus* extract and *Passiflora edulis* extract comprising Piceatannol, Scirpusin B, Scirpusin A, Cyperusphenol A and Cyperusphenol B, standardized to contain 6-10% w/w total stilbenes to achieve effects of (a) increased expression of PRDM16, PGC-1α and BMP7, (b) induce brown or beige or brite phenotype in white adipocyte depots, or (c) induce enhanced expression of mitochondrial uncoupling protein-1 to result in increased mitochondrial thermogenesis in differentiated brown adipocytes and beige or brite adipocytes.

2. The method as in claim 1, wherein mammals requiring enhanced energy expenditure is-selected from the group consisting of mammals in need of cold thermogenesis and increased endurance during physical activity and mammals with obesity.

3. A method of inhibition of adipogenesis in mammalian cellular systems, said method comprising step of bringing into contact mammalian adipocytes with a composition comprising *Cyperus rotundus* extract and *Passiflora edulis* extract comprising Piceatannol, Scirpusin B, Scirpusin A, Cyperusphenol A and Cyperusphenol B, standardized to contain 6-10% w/w total stilbenes to bring about inhibition in adipogenesis.

\* \* \* \* \*